(12) United States Patent
Girotto et al.

(10) Patent No.: US 11,596,475 B2
(45) Date of Patent: *Mar. 7, 2023

(54) SYSTEMS AND METHODS FOR ULTRASOUND IMAGE-GUIDED ABLATION ANTENNA PLACEMENT

(71) Applicant: Covidien LP, Mansfield, MA (US)

(72) Inventors: Darren G. Girotto, Louisville, CO (US); Kevin J. Frank, Louisville, CO (US)

(73) Assignee: Covidien LP, Mansfield, MA (US)

( * ) Notice: Subject to any disclaimer, the term of this patent is extended or adjusted under 35 U.S.C. 154(b) by 555 days.

This patent is subject to a terminal disclaimer.

(21) Appl. No.: 16/736,907

(22) Filed: Jan. 8, 2020

(65) Prior Publication Data

US 2020/0138516 A1 May 7, 2020

Related U.S. Application Data

(63) Continuation of application No. 15/342,157, filed on Nov. 3, 2016, now Pat. No. 10,548,666.
(Continued)

(51) Int. Cl.
*A61B 18/18* (2006.01)
*A61B 34/10* (2016.01)
(Continued)

(52) U.S. Cl.
CPC ........ *A61B 18/1815* (2013.01); *A61B 8/0841* (2013.01); *A61B 8/4254* (2013.01);
(Continued)

(58) Field of Classification Search
CPC ...... A61B 18/1815; A61B 2018/00577; A61B 2018/1823; A61B 2018/1861;
(Continued)

(56) References Cited

U.S. PATENT DOCUMENTS 6,106,460 A  8/2000 Panescu et al.
6,122,538 A  9/2000 Sliwa, Jr. et al.
(Continued)

FOREIGN PATENT DOCUMENTS

CN  102281819 A  12/2011
CN  103417293 A  12/2013
(Continued)

OTHER PUBLICATIONS

European Examination Report issued in corresponding Appl. No. EP 16199097.3 dated Jan. 12, 2021.
(Continued)

*Primary Examiner* — Michael F Peffley
*Assistant Examiner* — Amanda L Zink
(74) *Attorney, Agent, or Firm* — Carter, DeLuca & Farrell LLP

(57) ABSTRACT

Disclosed are devices, systems, and methods for generating a graphical user interface for use during a microwave ablation procedure, an exemplary method comprising receiving microwave ablation procedure configuration settings, receiving ultrasound image data from the ultrasound sensor, receiving the EM tracking data from the EM tracking system, determining a trajectory of the ablation probe based on the EM tracking data, and generating a graphical user interface showing a position and orientation of the ablation probe and the trajectory in relation to a plane of the ultrasound image data.

19 Claims, 13 Drawing Sheets

Related U.S. Application Data

(60) Provisional application No. 62/256,509, filed on Nov. 17, 2015.

(51) Int. Cl.

| | | |
|---|---|---|
| *A61B 8/08* | (2006.01) | |
| *A61B 8/00* | (2006.01) | |
| *A61B 34/20* | (2016.01) | |
| *A61B 34/00* | (2016.01) | |
| *A61B 18/00* | (2006.01) | |
| *A61B 90/00* | (2016.01) | |

(52) U.S. Cl.
CPC .............. *A61B 8/463* (2013.01); *A61B 34/10* (2016.02); *A61B 34/20* (2016.02); *A61B 34/25* (2016.02); *A61B 8/085* (2013.01); *A61B 2018/00577* (2013.01); *A61B 2018/1823* (2013.01); *A61B 2018/1861* (2013.01); *A61B 2034/107* (2016.02); *A61B 2034/2051* (2016.02); *A61B 2034/2063* (2016.02); *A61B 2090/378* (2016.02)

(58) Field of Classification Search
CPC ...... A61B 2034/107; A61B 2034/2051; A61B 2034/2063; A61B 2090/378; A61B 34/10; A61B 34/20; A61B 34/25; A61B 8/0841; A61B 8/085; A61B 8/463; A61B 8/4254
See application file for complete search history.

(56) References Cited

U.S. PATENT DOCUMENTS

| | | | |
|---|---|---|---|
| 6,216,029 B1 | 4/2001 | Paltieli | |
| 6,289,239 B1 | 9/2001 | Panescu et al. | |
| 6,478,793 B1* | 11/2002 | Cosman | A61B 34/20 606/49 |
| 6,540,679 B2 | 4/2003 | Slayton et al. | |
| 6,628,977 B2 | 9/2003 | Graumann et al. | |
| 6,788,969 B2 | 9/2004 | Dupree et al. | |
| 7,270,634 B2 | 9/2007 | Scampini et al. | |
| 7,343,195 B2 | 3/2008 | Strommer et al. | |
| 7,452,357 B2 | 11/2008 | Vlegele et al. | |
| 7,706,860 B2 | 4/2010 | McGee | |
| 7,860,548 B2 | 12/2010 | McIntyre et al. | |
| 8,123,691 B2 | 2/2012 | Mine et al. | |
| 8,228,347 B2 | 7/2012 | Beasley et al. | |
| 8,350,902 B2 | 1/2013 | Razzaque et al. | |
| 8,556,815 B2 | 10/2013 | Pelissier et al. | |
| 8,568,323 B2 | 10/2013 | Ichioka et al. | |
| 8,585,598 B2 | 11/2013 | Razzaque et al. | |
| 8,670,816 B2 | 3/2014 | Green et al. | |
| 8,690,776 B2 | 4/2014 | Razzaque et al. | |
| 8,731,264 B2 | 5/2014 | Kruecker et al. | |
| 8,750,568 B2* | 6/2014 | Frank | A61B 34/20 382/103 |
| 8,887,551 B2 | 11/2014 | Amit | |
| 8,900,225 B2 | 12/2014 | Bar-Tal et al. | |
| 8,906,010 B2 | 12/2014 | Edwards et al. | |
| 8,926,605 B2 | 1/2015 | McCarthy et al. | |
| 9,282,947 B2 | 3/2016 | Razzaque et al. | |
| 10,548,666 B2 | 2/2020 | Girotto et al. | |
| 2005/0033160 A1 | 2/2005 | Yamagata et al. | |
| 2005/0090746 A1 | 4/2005 | Ohtake | |
| 2007/0032723 A1* | 2/2007 | Glossop | A61B 18/18 600/424 |
| 2008/0033417 A1* | 2/2008 | Nields | A61B 18/1815 606/41 |
| 2009/0118613 A1 | 5/2009 | Krugman et al. | |
| 2009/0221908 A1 | 9/2009 | Glossop | |
| 2013/0197357 A1* | 8/2013 | Green | A61B 34/10 600/424 |
| 2014/0031674 A1 | 1/2014 | Newman et al. | |
| 2014/0142426 A1 | 5/2014 | Razzaque et al. | |
| 2015/0057774 A1* | 2/2015 | Boukhny | G05B 15/02 700/90 |
| 2015/0245819 A1 | 9/2015 | Yoshiara et al. | |
| 2016/0081653 A1 | 3/2016 | Masuda et al. | |
| 2016/0317231 A1 | 11/2016 | Girotto et al. | |

FOREIGN PATENT DOCUMENTS

| | | |
|---|---|---|
| JP | 2000500031 A | 1/2000 |
| JP | 2001340350 A | 12/2001 |
| JP | 2005118142 A | 5/2005 |
| JP | 2005169070 A | 6/2005 |
| JP | 2005253742 A | 9/2005 |
| JP | 2010187731 A | 9/2010 |
| JP | 2013220132 A | 10/2013 |
| JP | 2014501143 A | 1/2014 |
| JP | 2014113481 A | 6/2014 |
| JP | 2015198888 A | 11/2015 |

OTHER PUBLICATIONS

Canadian Office Action issued in corresponding application CA 2,948,280 dated Feb. 22, 2022 (5 pages).
International Search Report issued by the Japan Patent Office corresponding to International Patent Application No. PCT/US2016/030028; completed on Jul. 26, 2016 and dated Aug. 9, 2016 (8 pp.).
Japanese Office Action issued in corresponding application No. 2016-223095, dated Sep. 7, 2017.
Japanese Office Action for application No. 2016-223095 dated Dec. 19, 2017 (10 pages).
Notice of Allowance issued by the Japanese Patent Office dated Jun. 28, 2018, for Japanese Patent Application No. 2016-223095, with English translation.
Chinese Office Action issued in application No. 201611027154.5 dated Aug. 20, 2018, together with English language translation (20 pages).
Extended European Search Report issued by the European Patent Office, corresponding to Application No. 16199097.3, dated Mar. 22, 2017 (8 pages).

* cited by examiner

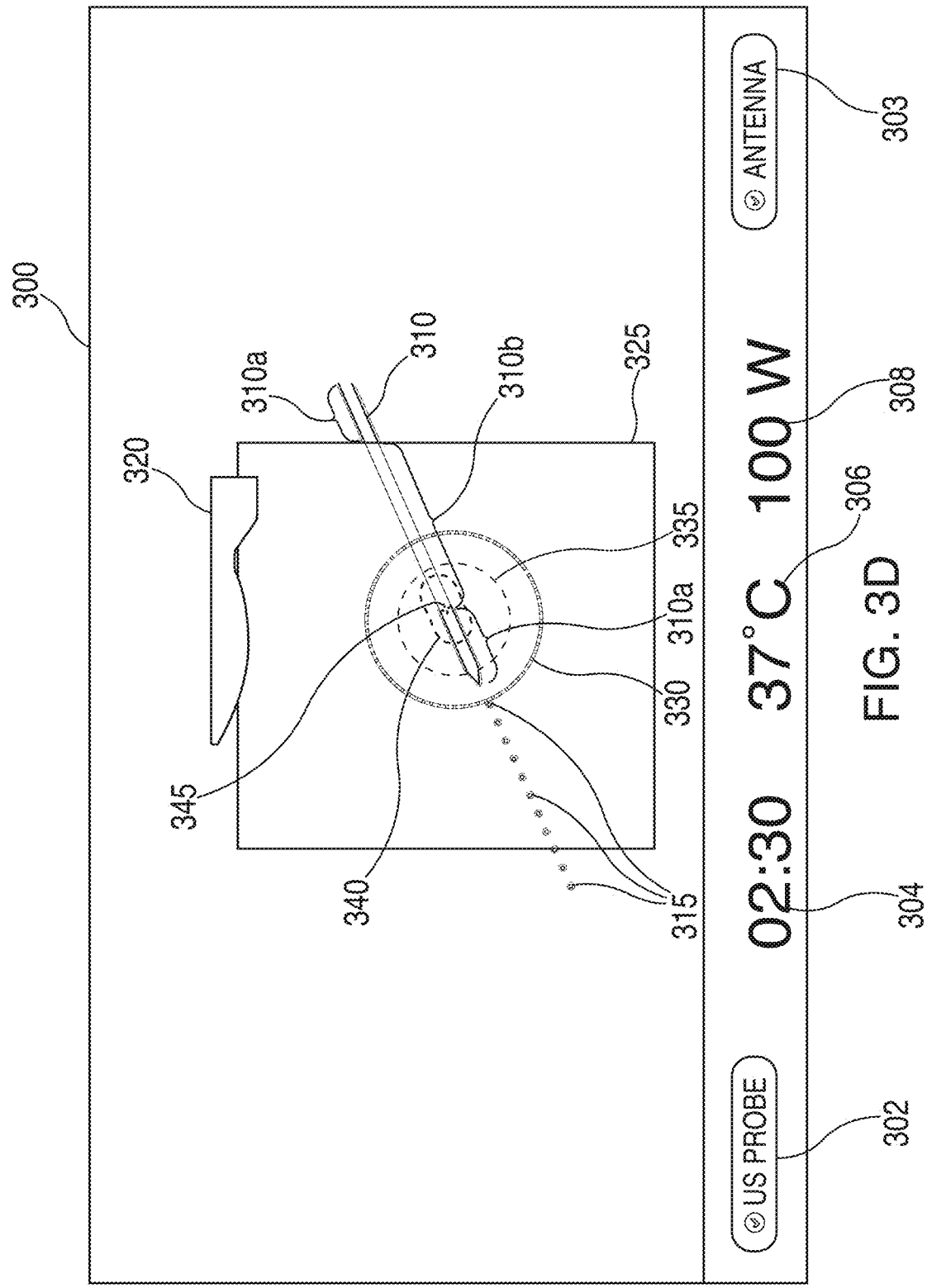

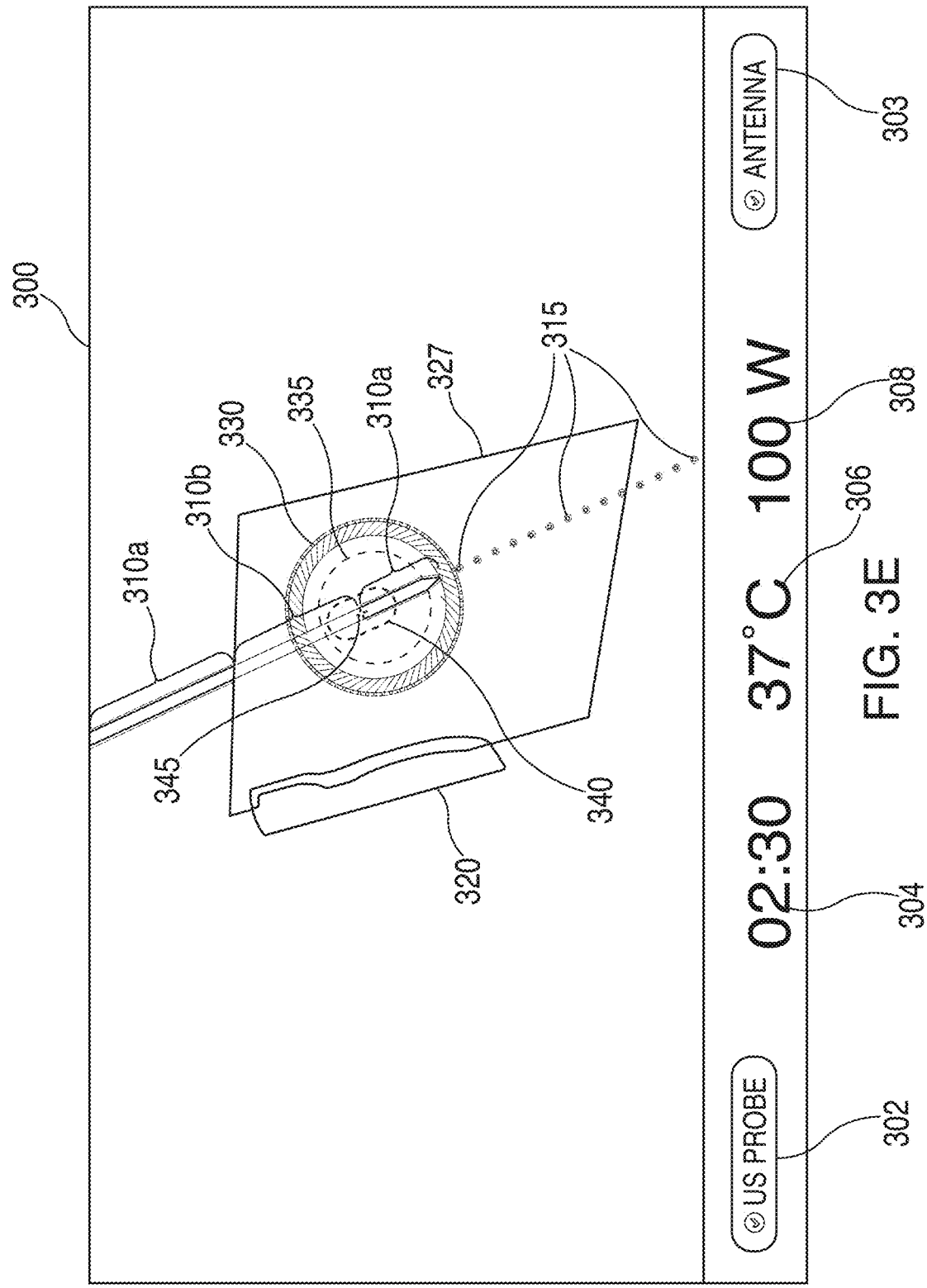

SYSTEMS AND METHODS FOR ULTRASOUND IMAGE-GUIDED ABLATION ANTENNA PLACEMENT

CROSS REFERENCE TO RELATED APPLICATIONS

The present application is a continuation of U.S. patent application Ser. No. 15/342,157, filed on Nov. 3, 2016, now U.S. Pat. No. 10,548,666, which claims the benefit of and priority to U.S. Provisional Patent Application No. 62/256,509, filed on Nov. 17, 2015, the entire contents of each of which are incorporated herein by reference.

BACKGROUND

1. Technical Field

The present disclosure relates to systems, methods, and devices for placing an ablation antenna using ultrasound image guidance.

2. Discussion of Related Art

When planning a treatment procedure, clinicians often rely on patient data including X-ray data, computed tomography (CT) scan data, magnetic resonance imaging (MRI) data, or other imaging data that allows the clinician to view the internal anatomy of a patient. The clinician utilizes the patient data to identify targets of interest and to develop strategies for accessing the targets of interest for the surgical procedure.

The use of CT images as a diagnostic tool has become routine and CT results are frequently the primary source of information available to a clinician regarding the size and location of a lesion, tumor or other similar target of interest. This information is used by the clinician for planning an operative procedure such as a biopsy or an ablation procedure, but is only available as "offline" information which must typically be memorized to the best of the clinician's ability prior to beginning a procedure. During a CT scan, a patient is digitally imaged and a CT image data volume is assembled. The CT image data may then be viewed by the clinician each of the axial, coronal and sagittal directions. A clinician reviews the CT image data slice by slice from each direction when attempting to identify or locate a target. It is often difficult, however, for the clinician to effectively plan a surgical ablation procedure based on the X-rays, CT images, or MRIs in their raw form.

SUMMARY

Systems and methods for planning and performing a microwave ablation treatment procedure are provided.

According to an aspect of the present disclosure, a system for performing a microwave ablation procedure comprises an electrosurgical generator, an ablation probe usable with the electrosurgical generator, an ultrasound sensor collecting ultrasound image data, an electromagnetic (EM) tracking system collecting EM tracking data about the positions of the ultrasound sensor and the ablation probe, and a computing device including a processor and a memory storing instructions which, when executed by the processor, cause the computing device to receive microwave ablation procedure configuration settings receive ultrasound image data from the ultrasound sensor, receive the EM tracking data from the EM tracking system, determine a trajectory of the ablation probe based on the EM tracking data, and generate a graphical user interface showing a position and orientation of the ablation probe and the trajectory in relation to a plane of the ultrasound image data.

In another aspect of the present disclosure, the instructions further cause the computing device to determine a projected ablation zone based on the received microwave ablation procedure configuration settings, and generating the graphical user interface further includes showing the projected ablation zone.

In a further aspect of the present disclosure, the instructions further cause the computing device to determine whether the position and orientation of the ablation probe has changed, and generate an updated graphical user interface showing the changed position and orientation of the ablation probe.

In another aspect of the present disclosure, the instructions further cause the computing device to determine whether the position and orientation of the ultrasound sensor has changed, and generate an updated graphical user interface showing the changed position and orientation of the ultrasound sensor.

In a further aspect of the present disclosure, the instructions further cause the computing device to determine an intersection between the ablation probe and the plane of the ultrasound image data, and generating the graphical user interface further includes showing an indicator of the intersection between the ablation probe and the plane of the ultrasound image data.

In another aspect of the present disclosure, the indicator is an obround shape showing an angle and directionality of the intersection between the ablation probe and the plane of the ultrasound image data.

In a further aspect of the present disclosure, the trajectory shown in the graphical user interface has a length approximately equal to a length of the ablation probe.

In another aspect of the present disclosure, the graphical user interface shows the position and orientation of the ablation probe and the trajectory as outlines such that the ultrasound image data is not obscured.

In a further aspect of the present disclosure, the instructions further cause the computing device to determine whether the microwave ablation procedure has started, and generate an updated graphical user interface showing an indicator of the progress of the ablation process.

According to an aspect of the present disclosure, a method of generating a graphical user interface for use during a microwave ablation procedure comprises receiving microwave ablation procedure configuration settings, receiving ultrasound image data from the ultrasound sensor, receiving the EM tracking data from the EM tracking system, determining a trajectory of the ablation probe based on the EM tracking data, and generating a graphical user interface showing a position and orientation of the ablation probe and the trajectory in relation to a plane of the ultrasound image data.

In another aspect of the present disclosure, the method further comprises determining a projected ablation zone based on the received microwave ablation procedure configuration settings, and generating the graphical user interface further includes showing the projected ablation zone.

In a further aspect of the present disclosure, the method further comprises determining whether the position and orientation of the ablation probe has changed, and generating an updated graphical user interface showing the changed position and orientation of the ablation probe.

In another aspect of the present disclosure, the method further comprises determining whether the position and orientation of the ultrasound sensor has changed, and generating an updated graphical user interface showing the changed position and orientation of the ultrasound sensor.

In a further aspect of the present disclosure, the method further comprises determining an intersection between the ablation probe and the plane of the ultrasound image data, and generating the graphical user interface further includes showing an indicator of the intersection between the ablation probe and the plane of the ultrasound image data.

In another aspect of the present disclosure, the indicator is an obround shape showing an angle and directionality of the intersection between the ablation probe and the plane of the ultrasound image data.

In a further aspect of the present disclosure, the trajectory shown in the graphical user interface has a length approximately equal to a length of the ablation probe.

In another aspect of the present disclosure, the graphical user interface shows the position and orientation of the ablation probe and the trajectory as outlines such that the ultrasound image data is not obscured.

In a further aspect of the present disclosure, the method further comprises determining whether the microwave ablation procedure has started, and generating an updated graphical user interface showing an indicator of the progress of the ablation process.

According to an aspect of the present disclosure, a non-transitory computer-readable storage medium stores instructions which, when executed by a processor, cause a computing device to receive microwave ablation procedure configuration settings, receive ultrasound image data from the ultrasound sensor, receive the EM tracking data from the EM tracking system, determine a trajectory of the ablation probe based on the EM tracking data, and generate a graphical user interface showing a position and orientation of the ablation probe and the trajectory in relation to a plane of the ultrasound image data.

Any of the above aspects and embodiments of the present disclosure may be combined without departing from the scope of the present disclosure.

BRIEF DESCRIPTION OF THE DRAWINGS

Objects and features of the presently disclosed system and method will become apparent to those of ordinary skill in the art when descriptions of various embodiments thereof are read with reference to the accompanying drawings, of which:

FIG. 3D is an illustration of another example graphical user interface which may be used during the procedure phase of a microwave ablation treatment in accordance with an embodiment of the present disclosure;

FIG. 3E is an illustration of another example graphical user interface which may be used during the procedure phase of a microwave ablation treatment in accordance with an embodiment of the present disclosure;

DETAILED DESCRIPTION

The present disclosure provides a system and method for planning and performing microwave ablation surgical treatment. The system presents a clinician with a streamlined method of treatment planning from the initial patient selection through a process of target identification and selection, target sizing, treatment zone sizing, entry point and route selection to create a pathway to the target, and treatment plan review. The treatment plan may then be used as a guide during the performance of the surgical procedure, where the system is configured to track the position of surgical tools inside the patient and give the clinician a real-time view of the position of the tools in relation to the target and the pre-planned pathway toward the target. The system also presents a clinician with the capability to compare and contrast pre-operative and post-operative CT image data to assess the outcome of a surgical treatment procedure that has been performed.

Although the present disclosure will be described in terms of specific illustrative embodiments, it will be readily apparent to those skilled in this art that various modifications, rearrangements and substitutions may be made without departing from the spirit of the present disclosure. The scope of the present disclosure is defined by the claims appended hereto.

Microwave ablation treatment, according to the present disclosure, is generally divided into two phases: (1) a planning phase, and (2) a procedure phase. The planning phase of microwave ablation treatment is more fully described in co-pending patent application Ser. No. 14/821,950 entitled TREATMENT PROCEDURE PLANNING SYSTEM AND METHOD, filed on Aug. 11, 2014 by Bharadwaj et al., the contents of which is hereby incorporated by reference in its entirety. The alternative planning and a procedure phase are more fully described below.

A microwave ablation planning and procedure system according to the present disclosure may be a unitary system configured to perform both the planning phase and the procedure phase, or the system may include separate devices and software programs for the various phases. An example of the latter may be a system wherein a first computing device with one or more specialized software programs is used during the planning phase, and a second computing device with one or more specialized software programs may import data from the first computing device to be used during the procedure phase.

Figure 1:
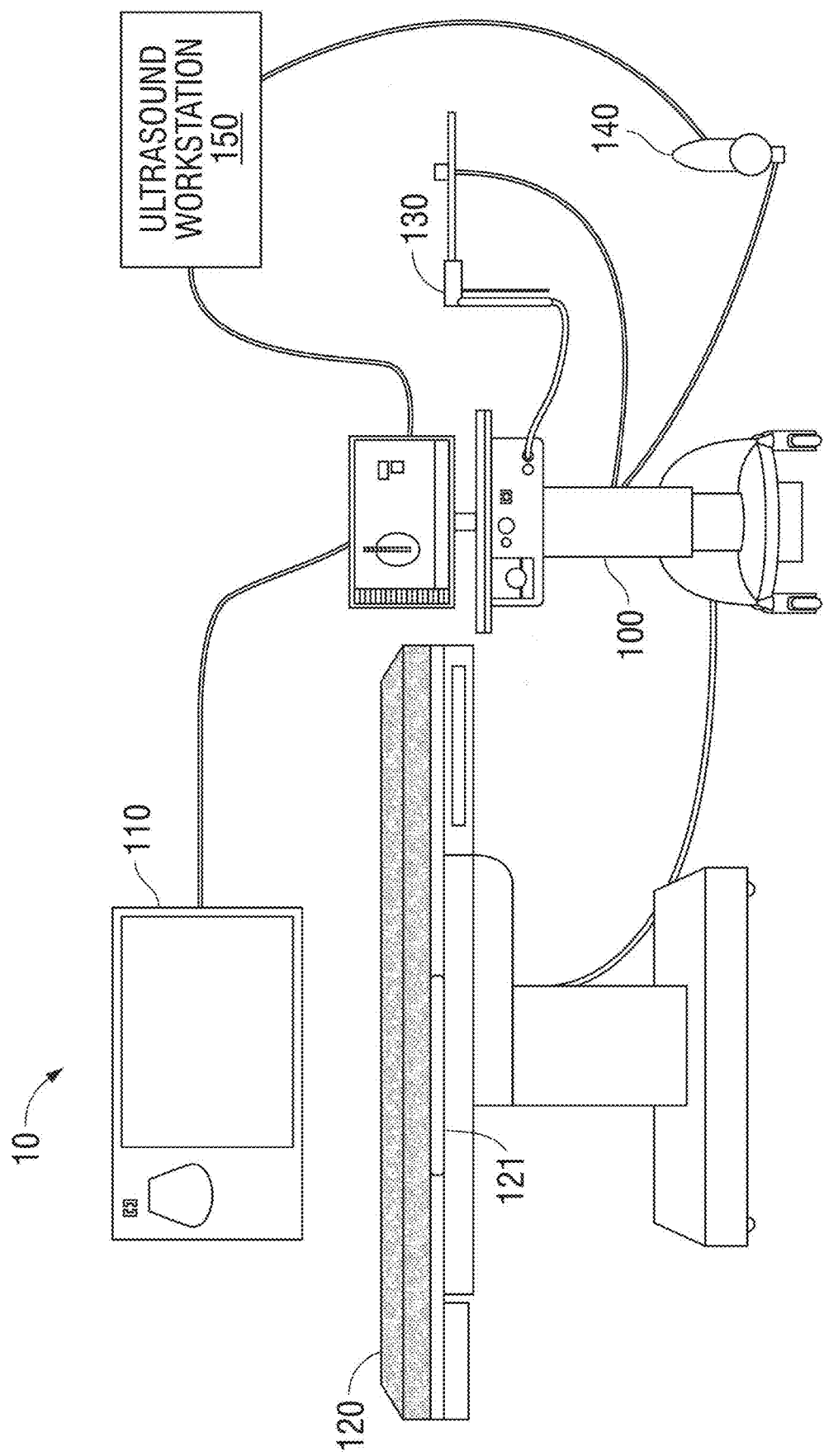
FIG. 1 is a schematic diagram of a microwave ablation planning and procedure system in accordance with an illustrative embodiment of the present disclosure.

Referring now to FIG. 1, the present disclosure is generally directed to a treatment system 10, which includes a computing device 100, a display 110, a table 120, an ablation probe 130, an ultrasound imager 140, and an ultrasound workstation 150. Computing device 100 may be, for example, a laptop computer, desktop computer, tablet computer, or other similar device. Computing device 100 may be configured to control an electrosurgical generator, a peristaltic pump, a power supply, and/or any other accessories and peripheral devices relating to, or forming part of, system 10. Display 110 is configured to output instructions, images, and messages relating to the performance of the microwave ablation procedure. Table 120 may be, for example, an operating table or other table suitable for use during a surgical procedure, which includes an electromagnetic (EM) field generator 121. EM field generator 121 is used to generate an EM field during the microwave ablation procedure and forms part of an EM tracking system which is used to track the positions of surgical instruments within the body of a patient. EM field generator 121 may include various components, such as a specially designed pad to be placed under, or integrated into, an operating table or patient bed. An example of such an EM tracking system is the AURORA™ system sold by Northern Digital Inc. Ablation probe 130 is a surgical instrument having a microwave ablation antenna which is used to ablate tissue. While the present disclosure describes the use of system 10 in a surgical environment, it is also envisioned that some or all of the components of system 10 may be used in alternative settings, for example, an imaging laboratory and/or an office setting.

In addition to the EM tracking system, the surgical instruments may also be visualized by using ultrasound imaging. Ultrasound imager 140, such as an ultrasound wand, may be used to image the patient's body during the microwave ablation procedure to visualize the location of the surgical instruments, such as ablation probe 130, inside the patient's body. Ultrasound imager 140 may have an EM tracking sensor embedded within or attached to the ultrasound wand, for example, a clip-on sensor or a sticker sensor. As described further below, ultrasound imager 140 may be positioned in relation to ablation probe 130 such that ablation probe 130 is at an angle to the ultrasound image plane, thereby enabling the clinician to visualize the spatial relationship of ablation probe 130 with the ultrasound image plane and with objects being imaged. Further, the EM tracking system may also track the location of ultrasound imager 140. In some embodiments, one or more ultrasound sensors 140 may be placed inside the body of the patient. EM tracking system may then track the location of such ultrasound sensors 140 and ablation probe 130 inside the body of the patient.

Various other surgical instruments or surgical tools, such as ligasure devices, surgical staples, etc., may also be used during the performance of a microwave ablation treatment procedure. Ablation probe 130 is used to ablate a lesion or tumor (hereinafter referred to as a "target") by using electromagnetic radiation or microwave energy to heat tissue in order to denature or kill cancerous cells. The construction and use of a system including such an ablation probe 130 is more fully described in co-pending patent application Ser. No. 14/828,682 entitled MICROWAVE ABLATION SYSTEM, filed on Aug. 26, 2014, by Dickhans, co-pending patent application publication no. 2014/0046315 entitled MICROWAVE ABLATION CATHETER AND METHOD OF UTILIZING THE SAME, filed on Mar. 15, 2013, by Latkow et al., and co-pending patent application publication no. 2014/0276739 entitled MICROWAVE ENERGY-DELIVERY DEVICE AND SYSTEM, filed on Mar. 15, 2013, by Brannan et al., the contents of all of which is hereby incorporated by reference in its entirety.

The location of ablation probe 130 within the body of the patient may be tracked during the surgical procedure. An example method of tracking the location of ablation probe 130 is by using the EM tracking system, which tracks the location of ablation probe 130 by tracking sensors attached to or incorporated in ablation probe 130. Various types of sensors may be used, such as a printed sensor, the construction and use of which is more fully described in co-pending provision patent application No. 62/095,563 filed Dec. 22, 2014, the entire contents of which is incorporated herein by reference. Prior to starting the procedure, the clinician is able to verify the accuracy of the tracking system.

Figure 2:
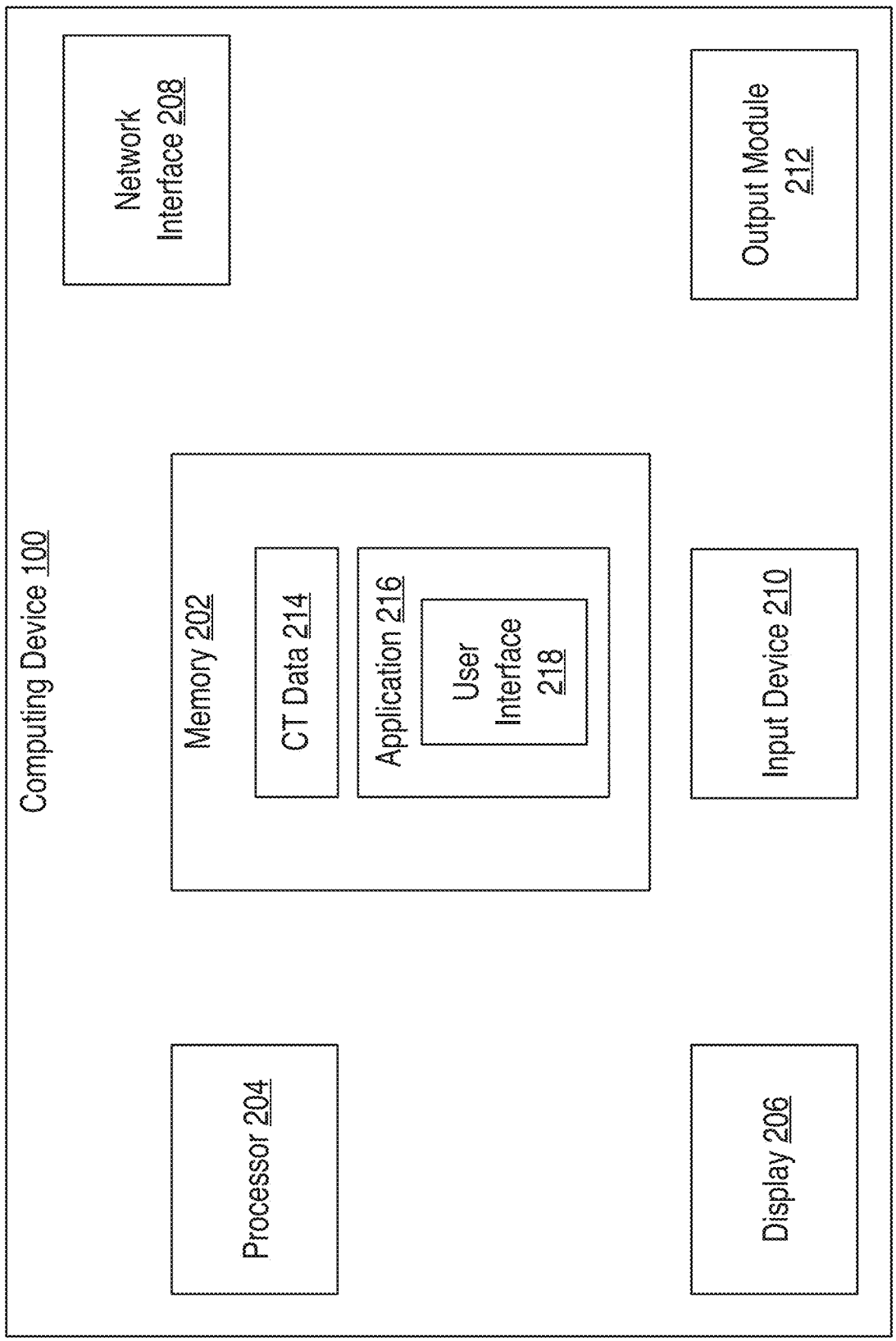
FIG. 2 is a schematic diagram of a computing device which forms part of the microwave ablation planning and procedure system of FIG. 1 in accordance with an embodiment of the present disclosure.

Turning now to FIG. 2, there is shown a system diagram of computing device 100. Computing device 100 may include memory 202, processor 204, display 206, network interface 208, input device 210, and/or output module 212.

Memory 202 includes any non-transitory computer-readable storage media for storing data and/or software that is executable by processor 204 and which controls the operation of computing device 100. In an embodiment, memory 202 may include one or more solid-state storage devices such as flash memory chips. Alternatively or in addition to the one or more solid-state storage devices, memory 202 may include one or more mass storage devices connected to the processor 204 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 204. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by computing device 100.

Memory 202 may store application 216 and/or CT data 214. Application 216 may, when executed by processor 204, cause display 206 to present user interface 218.

Processor 204 may be a general purpose processor, a specialized graphics processing unit (GPU) configured to perform specific graphics processing tasks while freeing up the general purpose processor to perform other tasks, and/or any number or combination of such processors.

Display 206 may be touch sensitive and/or voice activated, enabling display 206 to serve as both an input and output device. Alternatively, a keyboard (not shown), mouse (not shown), or other data input devices may be employed.

Network interface 208 may be configured to connect to a network such as a local area network (LAN) consisting of a wired network and/or a wireless network, a wide area network (WAN), a wireless mobile network, a Bluetooth network, and/or the internet. For example, computing device 100 may receive computed tomographic (CT) image data of a patient from a server, for example, a hospital server, internet server, or other similar servers, for use during surgical ablation planning. Patient CT image data may also be provided to computing device 100 via a removable memory 202. Computing device 100 may receive updates to its software, for example, application 216, via network interface 208. Computing device 100 may also display notifications on display 206 that a software update is available.

Input device 210 may be any device by means of which a user may interact with computing device 100, such as, for example, a mouse, keyboard, foot pedal, touch screen, and/or voice interface.

Output module 212 may include any connectivity port or bus, such as, for example, parallel ports, serial ports, universal serial busses (USB), or any other similar connectivity port known to those skilled in the art.

Application 216 may be one or more software programs stored in memory 202 and executed by processor 204 of computing device 100. As will be described in more detail below, during the planning phase, application 216 guides a clinician through a series of steps to identify a target, size the target, size a treatment zone, and/or determine an access route to the target for later use during the procedure phase. In some embodiments, application 216 is loaded on computing devices in an operating room or other facility where surgical procedures are performed, and is used as a plan or map to guide a clinician performing a surgical procedure, but without any feedback from ablation probe 130 used in the procedure to indicate where ablation probe 130 is located in relation to the plan. In other embodiments, system 10 provides computing device 100 with data regarding the location of ablation probe 130 within the body of the patient, such as by EM tracking, which application 216 may then use to indicate on the plan where ablation probe 130 are located.

Application 216 may be installed directly on computing device 100, or may be installed on another computer, for example a central server, and opened on computing device 100 via network interface 208. Application 216 may run natively on computing device 100, as a web-based application, or any other format known to those skilled in the art. In some embodiments, application 216 will be a single software program having all of the features and functionality described in the present disclosure. In other embodiments, application 216 may be two or more distinct software programs providing various parts of these features and functionality. For example, application 216 may include one software program for use during the planning phase, and a second software program for use during the procedure phase of the microwave ablation treatment. In such instances, the various software programs forming part of application 216 may be enabled to communicate with each other and/or import and export various settings and parameters relating to the microwave ablation treatment and/or the patient to share information. For example, a treatment plan and any of its components generated by one software program during the planning phase may be stored and exported to be used by a second software program during the procedure phase.

Application 216 communicates with a user interface 218 which generates a user interface for presenting visual interactive features to a clinician, for example, on display 206 and for receiving clinician input, for example, via a user input device. For example, user interface 218 may generate a graphical user interface (GUI) and output the GUI to display 206 for viewing by a clinician. Examples of the GUI are described below with reference to FIGS. 3A-3E and 4.

Computing device 100 is linked to display 110, thus enabling computing device 100 to control the output on display 110 along with the output on display 206. Computing device 100 may control display 110 to display output which is the same as or similar to the output displayed on display 206. For example, the output on display 206 may be mirrored on display 100. Alternatively, computing device 100 may control display 110 to display different output from that displayed on display 206. For example, display 110 may be controlled to display guidance images and information during the microwave ablation procedure, while display 206 is controlled to display other output, such as configuration or status information.

As used herein, the term "clinician" refers to any medical professional (i.e., doctor, surgeon, nurse, or the like) or other user of the treatment planning system 10 involved in planning, performing, monitoring and/or supervising a medical procedure involving the use of the embodiments described herein.

Figure 3A:
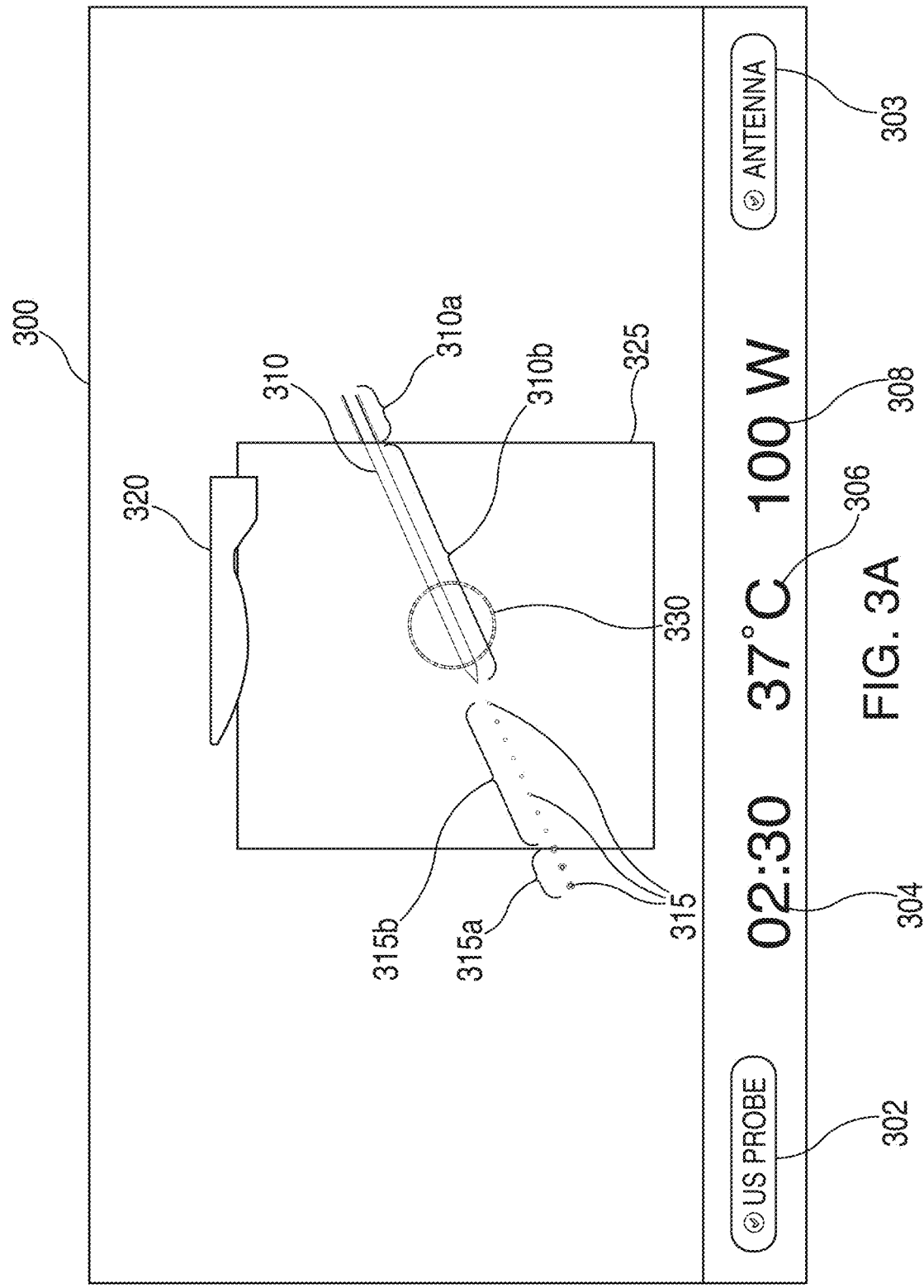
FIG. 3A is an illustration of an example graphical user interface which may be used during the procedure phase of a microwave ablation treatment in accordance with an embodiment of the present disclosure.

Turning now to FIG. 3A, there is shown an example GUI 300 generated by user interface 218 which may be presented by computing device 100 on display 206 and/or display 110. GUI 300 includes graphical representation of an ablation antenna 310 corresponding to ablation probe 130, a graphical representation of an ultrasound wand 320 corresponding to ultrasound imager 140, a graphical representation of a trajectory 315 of ablation probe 130, an ultrasound image plane 325, and a projected ablation zone indicator 330 showing a projected ablation zone as configured for the current ablation procedure. Ultrasound image plane 325 will include an ultrasound image (not shown here for the purpose of more clearly depicting the elements being described) based on ultrasound image data captured by ultrasound imager 140. GUI 300 further includes an US probe indicator 302 and antenna indicator 303 that indicates whether ultrasound imager 140 and ablation probe 130 are connected to computing device 100 and system 10. GUI 300 also includes indicators of a time 304, temperature 306, and wattage 308 configured for the current ablation procedure.

Trajectory 315 shows the trajectory at which ablation probe 130 is being navigated inside the patient's body. The length of trajectory 315 corresponds to the length of ablation probe 130. Likewise, the width of trajectory 315 corresponds to the width of ablation probe 130. Thus, when positioning ablation probe 130 and ultrasound imager 140 outside the patient's body, trajectory 315 will show the distance ablation probe 130 can be navigated into the patient's body. As such, the clinician can determine whether ablation probe 130 can reach the target tissue inside the patient's body before inserting ablation probe 130 into the patient's body.

GUI 300 may depict ablation antenna 310 and trajectory 315 as outlines, such that the ultrasound image displayed on ultrasound image plane 325 is not obscured by ablation antenna 310 and trajectory 315. GUI 300 further depicts ablation antenna 310 and trajectory 315 in relation to ultrasound image plane 325. That is, when ablation probe 130 does not intersect ultrasound image plane 325, ablation antenna 310 is depicted as shadowed (e.g. dimmed or greyed-out). For example, as shown in FIG. 3A, ablation antenna 310 is depicted in a shadowed section 310b for the portion of ablation antenna 310 displayed behind ultrasound image plane 325. Likewise, trajectory 315 is depicted as a shadowed section 315b for the portion of trajectory 315 that is behind ultrasound image plane 325. In contrast, the portion of the trajectory 315a which is in front of ultrasound image plane 325 is shown as regular (of normal brightness and not shadowed or dimmed).

Figure 3B:
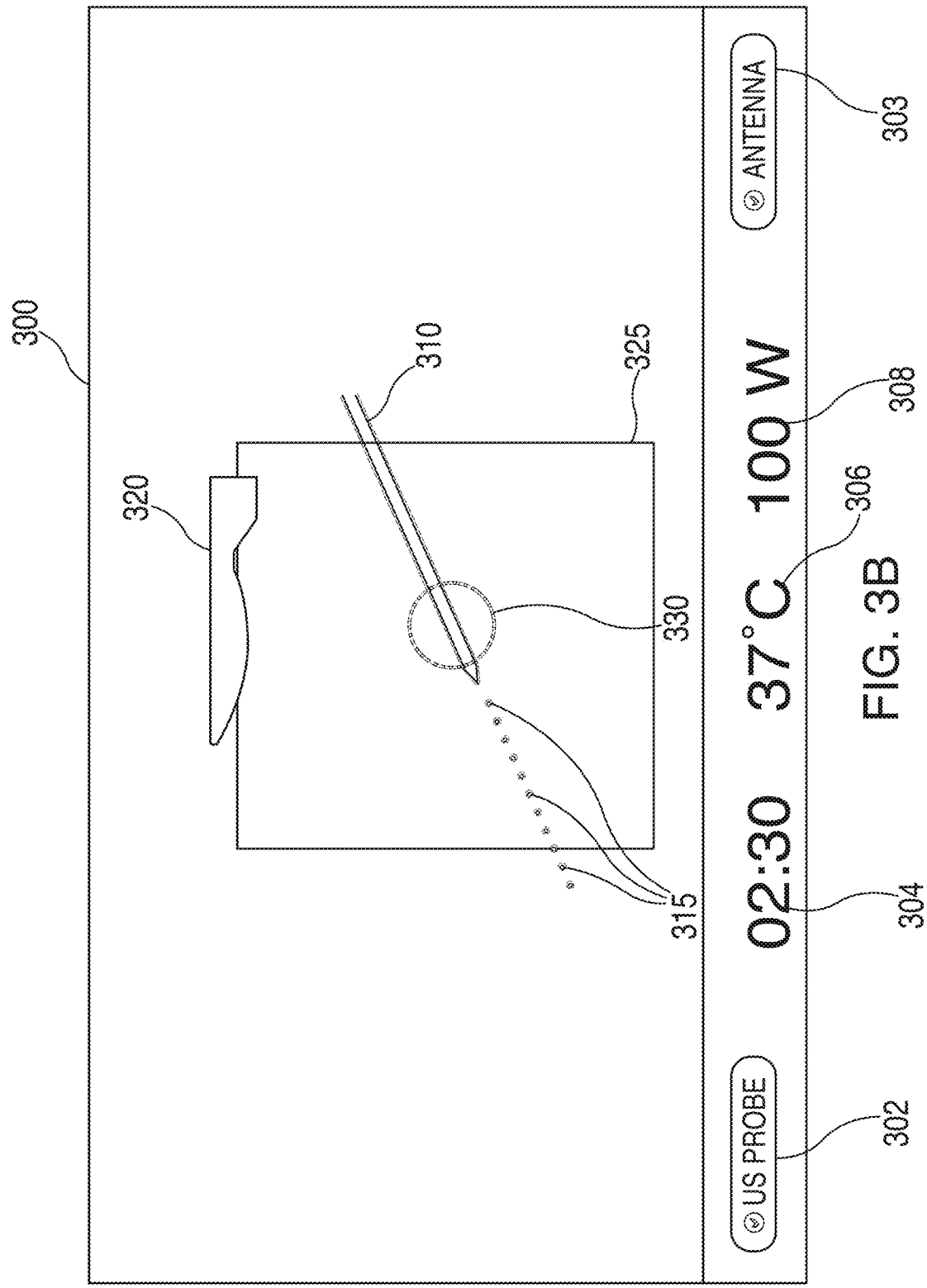
FIG. 3B is an illustration of another example graphical user interface which may be used during the procedure phase of a microwave ablation treatment in accordance with an embodiment of the present disclosure.

While FIG. 3A shows an example where all of ablation antenna 310 and trajectory 315 are behind ultrasound image plane 325, FIG. 3B shows an example where all of ablation antenna 310 and trajectory 315 are in front of ultrasound image plane 325. That is, ablation probe 130 is located entirely in front of, and does not intersect, the plane of the image generated by ultrasound imager 140.

Figure 3C:
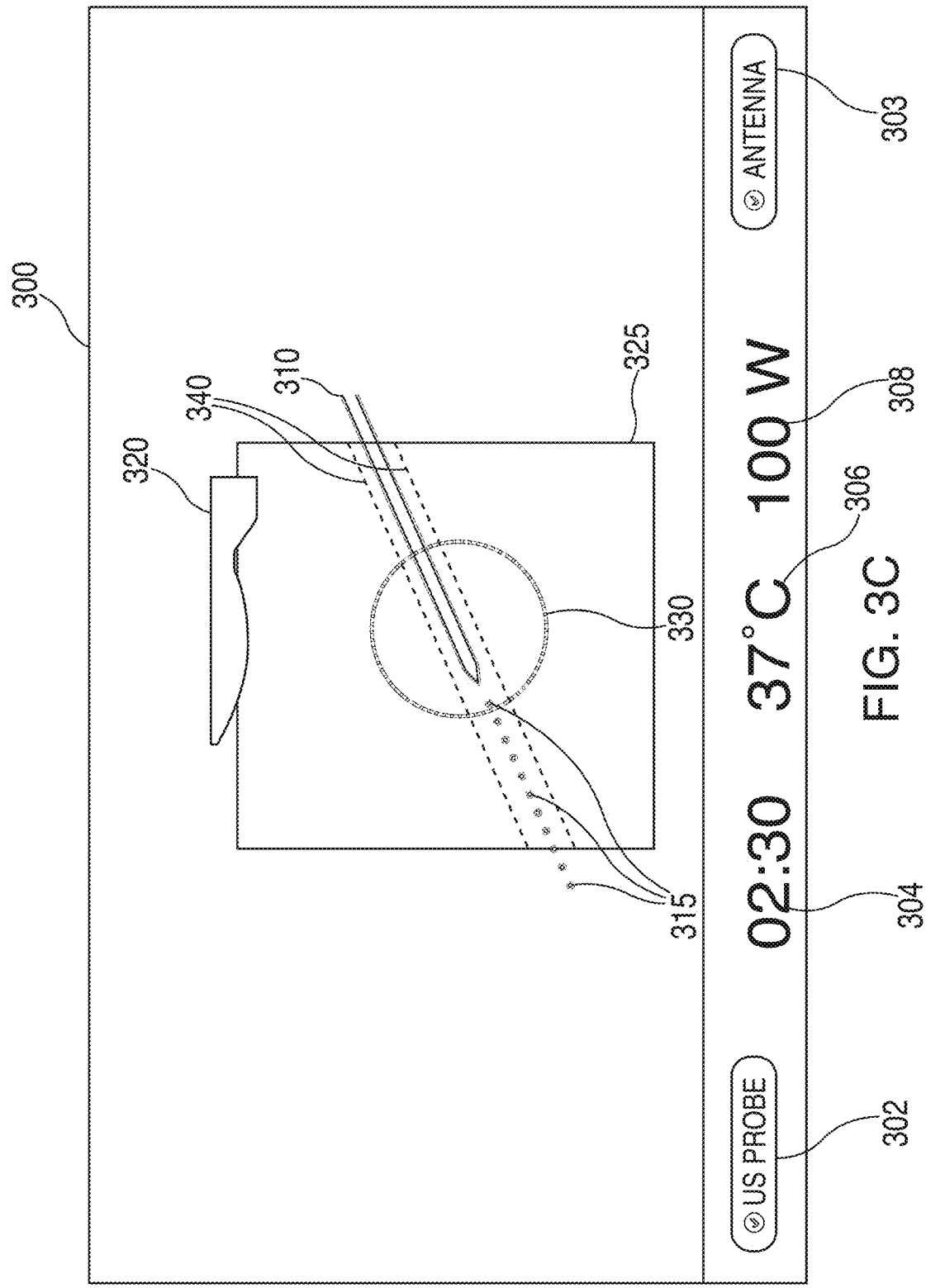
FIG. 3C is an illustration of another example graphical user interface which may be used during the procedure phase of a microwave ablation treatment in accordance with an embodiment of the present disclosure.

FIG. 3C shows another example GUI 300 generated by user interface 218 which may be displayed by computing device 100 on display 206 and/or display 110. FIG. 3C includes many of the same elements as FIGS. 3A and 3B. Those elements are identified using the same reference numerals as in FIGS. 3A and 3B, and will not be described again for purpose of brevity.

FIG. 3C shows an example where ablation antenna 310 is co-planar with ultrasound image plane 325. The area of intersection between plane of ablation antenna 310 and ultrasound image plane 325 is indicated by an obround 340. Because ablation antenna 310 is co-planar with ultrasound image plane 325, obround 340 is shown as two parallel lines on either side of ablation antenna 310 and trajectory 315.

FIG. 3D shows an example where ablation antenna 310 intersects ultrasound image plane 325. Unlike in FIG. 3C, where ablation antenna 310 is co-planar with ultrasound image plane 325 and obround 340 extends the length of ablation antenna 310 and trajectory 315, in FIG. 3D, obround 340 appears elliptical around the area of intersection between ablation antenna 310 and ultrasound image plane 325. The length and position of obround 340 is determined by the angle of intersection between ablation antenna 310 and ultrasound image plane 325. That is, obround 340 shows the direction and acuteness of the angle of intersection between ablation antenna 310 and ultrasound image plane 325. The point of intersection between ablation antenna 310 and ultrasound image plane 325 is shown by intersection indicator 345.

GUI 300 may further show an ablation progress indicator 335 after computing device 110 determines that the ablation procedure has been started. Ablation progress indicator 335 shows the progress of the ablation procedure being performed. Ablation progress indicator 335 will start close to ablation antenna 310 and move out toward projected ablation zone indicator 330 as the ablation procedure proceeds.

FIG. 3E shows another example GUI 300 generated by user interface 218 which may be displayed by computing device 100 on display 206 and/or display 110. FIG. 3E includes many of the same elements as FIGS. 3A-3D. Those elements are identified using the same reference numerals as in FIGS. 3A-3D and will not be described again for purpose of brevity.

FIGS. 3A-3D show ultrasound image plane 325 in which the orientation of ultrasound wand 320 and ultrasound image plane 325 are maintained in a fixed orientation normal to GUI 300. FIG. 3E, in contrast, depicts ultrasound wand 320 and an ultrasound image plane 327 according to an orientation of ultrasound imager 140 within an EM field generated by EM field generator 121. Thus, when the clinician moves ultrasound imager 140, the depiction of ultrasound wand 320 and ultrasound image plane 327 in GUI 300 changes according to the movement and angle of ultrasound imager 140 within the EM field, thereby providing a perspective view of the ablation zone and the position of ablation probe 130 therein.

GUI 300 may further include a perspective view area configured to correspond to a portion of the EM field that includes the treatment zone. For example, the patient may be positioned on table 120 such that the EM field generated by EM field generator 121 includes the treatment zone. Computing device 100 may then automatically and/or with assistance from the clinician select a portion of the EM field that includes the treatment zone, and may configure application 216 and/or GUI 300 to depict ablation antenna 310, ultrasound wand 320, ultrasound image plane 327, and the various other elements described above, in the perspective view area based on their detected and/or determined positions within the EM field. For example, ultrasound image plane 327 and ultrasound wand 320 may only be depicted in the perspective view area when ultrasound imager 140 is detected to be positioned within the portion of the EM field that is configured to be displayed in the perspective view area of GUI 300. Likewise, ablation antenna 310 may only be depicted in the perspective view area when ablation probe 130 is detected to be positioned within the portion of the EM field that is configured to be displayed in the perspective view area of GUI 300. Thus, when ultrasound imager 140 and/or ablation probe 130 are not in the portion of the EM field that is configured to be displayed in the perspective view area of GUI 300, GUI 300 will not display ultrasound wand 320, ultrasound image plane 327, and/or ablation antenna 310 in the perspective view area. The portion of the EM field that is configured to be displayed in the perspective view area of GUI 300 may be adjusted during the ablation procedure, such as by moving and/or zooming in and out.

As depicted in FIG. 3E, ultrasound imager 140 is rotated approximately 90° to the left and obliquely to the plane of the portion of the EM field shown in the perspective view area of GUI 300. These differences in orientation assist the clinician in understanding how movement of ultrasound imager 140 affects both ultrasound image plane 327 and ultrasound image plane 325. As depicted in FIG. 3E, projected ablation zone indicator 330 and/or progress indicator 335 may be three-dimensional (3D) projections. This 3D projection of either projected ablation zone indicator 330 and/or progress indicator 335 provides greater understanding of how the ablation zone interacts with all tissue and other structures in the ablation zone, and, during treatment, depicts how energy is being absorbed in all directions. Further, these features allow the clinician to sweep across ablation probe 130 to ascertain with greater clarity the effects of the ablation treatment on the treatment zone.

Figure 4:
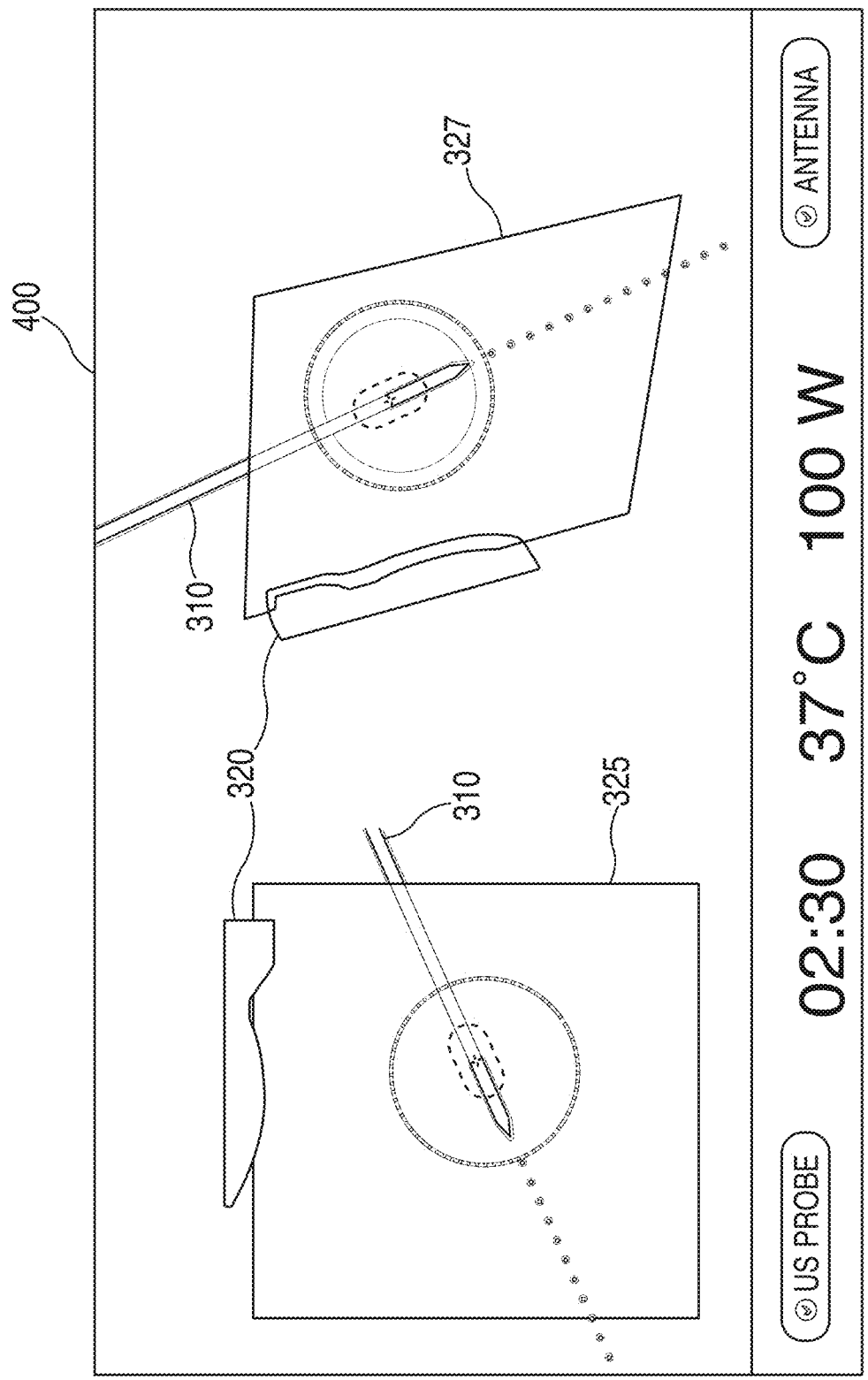
FIG. 4 is an illustration of another example graphical user interface which may be used during the procedure phase of a microwave ablation treatment in accordance with an embodiment of the present disclosure.

FIG. 4 shows an example GUI 400 generated by user interface 218 which may be displayed by computing device 100 on display 206 and/or display 110. FIG. 4 includes many of the same elements as FIGS. 3A-3E. Those elements are identified using the same reference numerals as in FIGS. 3A-3E and will not be described again for purpose of brevity.

GUI 400 includes side-by-side depictions of ultrasound image plane 325, which is displayed normal to GUI 300, as shown in FIGS. 3A-3D, and ultrasound image plane 327, which is shown relative to the placement of ultrasound imager 140 within the EM field generated by EM field generator 121.

Figure 5:
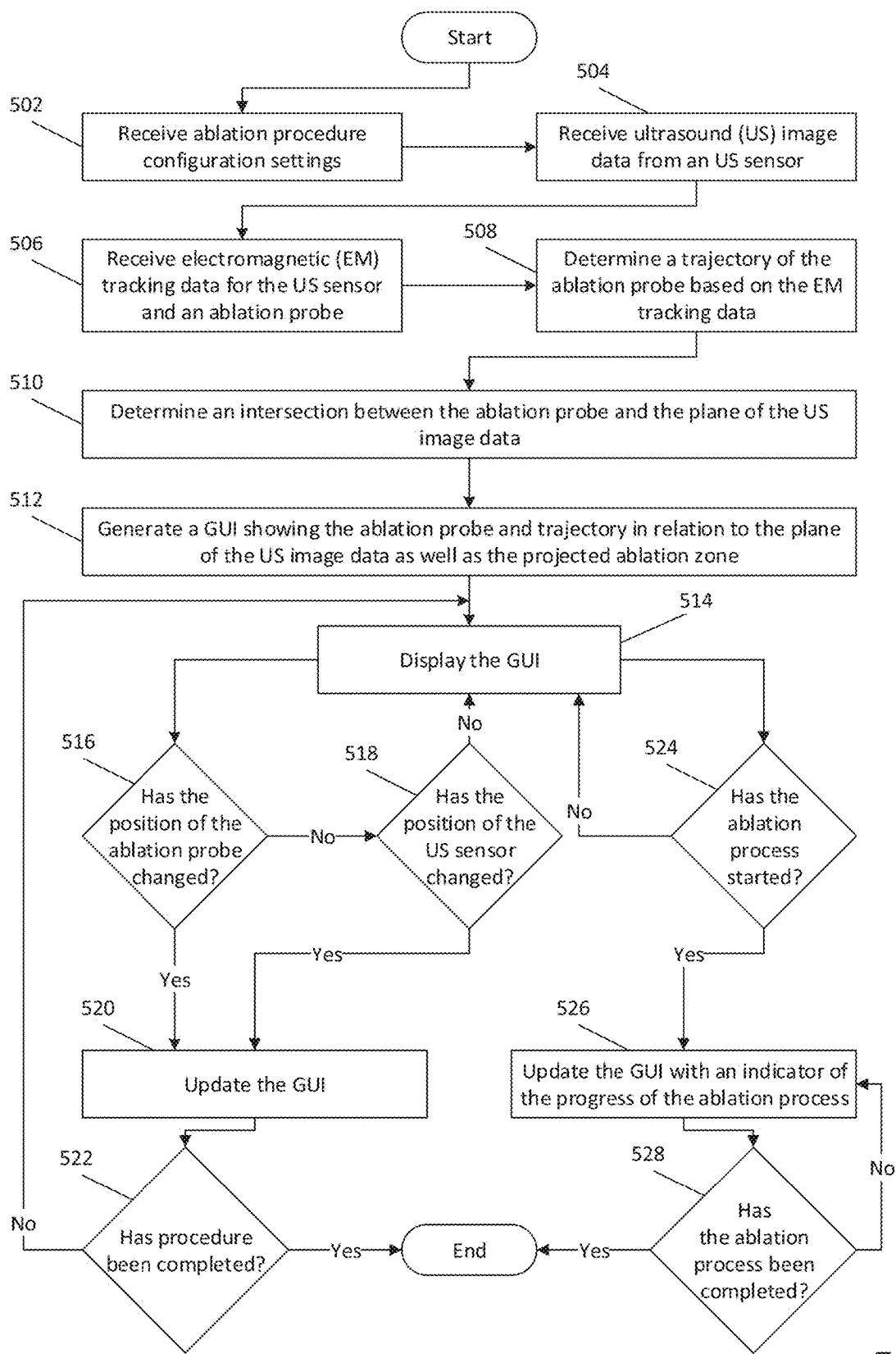
FIG. 5 is a flow chart of an example method of generating the graphical user interface of FIGS. 3A-E and/or FIG. 4, according to an embodiment of the present disclosure.

Turning now to FIG. 5, there is shown a flowchart of an example method for performing a microwave ablation procedure according to an embodiment of the present disclosure. At step 502, computing device 100 receives ablation procedure configuration settings. The settings may be entered manually by a clinician performing the ablation procedure, or may be preloaded from a preconfigured configuration settings file that was previously entered by the clinician. The ablation settings may be based on a particular treatment profile specific to the patient and/or the type of tissue sought to be ablated. The ablation settings may include an ablation time, temperature, and wattage. Once received, GUI 300 will display these ablation settings at indicators 304, 306, and 308, respectively. Further details about the planning phase of microwave ablation treatment is more fully described in co-pending provisional patent application Ser. No. 14/821,950 entitled TREATMENT PROCEDURE PLANNING SYSTEM AND METHOD.

Then, at step 504, computing device 100 receives ultrasound image data from ultrasound imager 140. The ultrasound image data may be relayed from ultrasound workstation 150. Next, or concurrently with step 504, computing device 100 receives EM tracking data from the EM tracking system for ultrasound imager 140 and ablation probe 130 at step 506.

Thereafter, at step 508, computing device 100 determines a trajectory of ablation probe 130 based on the EM tracking data. Next, at step 510, computing device 100 determines an intersection between ablation probe 130, or the trajectory of ablation probe 130, and the plane of the ultrasound image data received from ultrasound imager 140. Thereafter, at step 512, computing device 100 generates a GUI showing ablation antenna 310 and trajectory 315 in relation to ultrasound image plane 325, which is based on the ultrasound image data received from ultrasound imager 140, as well as the projected ablation zone 330, as shown in FIGS. 3A-3E and 4, described above. Next, at step 514, computing device 100 displays the GUI on display 206 and/or display 110.

Next, at step 516, computing device determines whether the position of ablation probe 130 has changed. If yes, computing device 100 updates the GUI at step 520. If not, computing device 100 determines, at step 518, whether the position of ultrasound imager 140 has changed. If yes, computing device 100 updates the GUI at step 520. If not, computing device continues displaying the GUI unchanged at step 514. Steps 516 and 518 may be performed interchangeably and/or concurrently, and will be performed iteratively throughout the ablation procedure.

After updating the GUI, computing device 100 determines, at step 522, whether the ablation procedure is complete. If yes, processing ends. If not, computing device displays the GUI, and processing returns to step 514.

Simultaneously with step 516, at step 524, computing device 100 determines whether the ablation process has started. If yes, computing device 100, at step 526, updates the GUI with an indicator of the progress of the ablation process, for example, indicator 335 shown in FIGS. 3D and 3E. Thereafter, at step 528, computing device 100 determines whether the ablation process has been completed. If yes, processing ends. If not, processing returns to step 526, where the GUI is iteratively updated based on the progress of the ablation procedure.

Turning now to FIGS. 6A-6D, there are shown another example GUI 600 generated by user interface 218 which may be presented by computing device 100 on display 206 and/or display 110. GUI 600 includes many of the same elements as described above with reference to FIGS. 3A-3E. Such elements are identified by the same reference numerals as described above, and therefore will not be described in detail again for purpose of brevity.

Figure 6A:
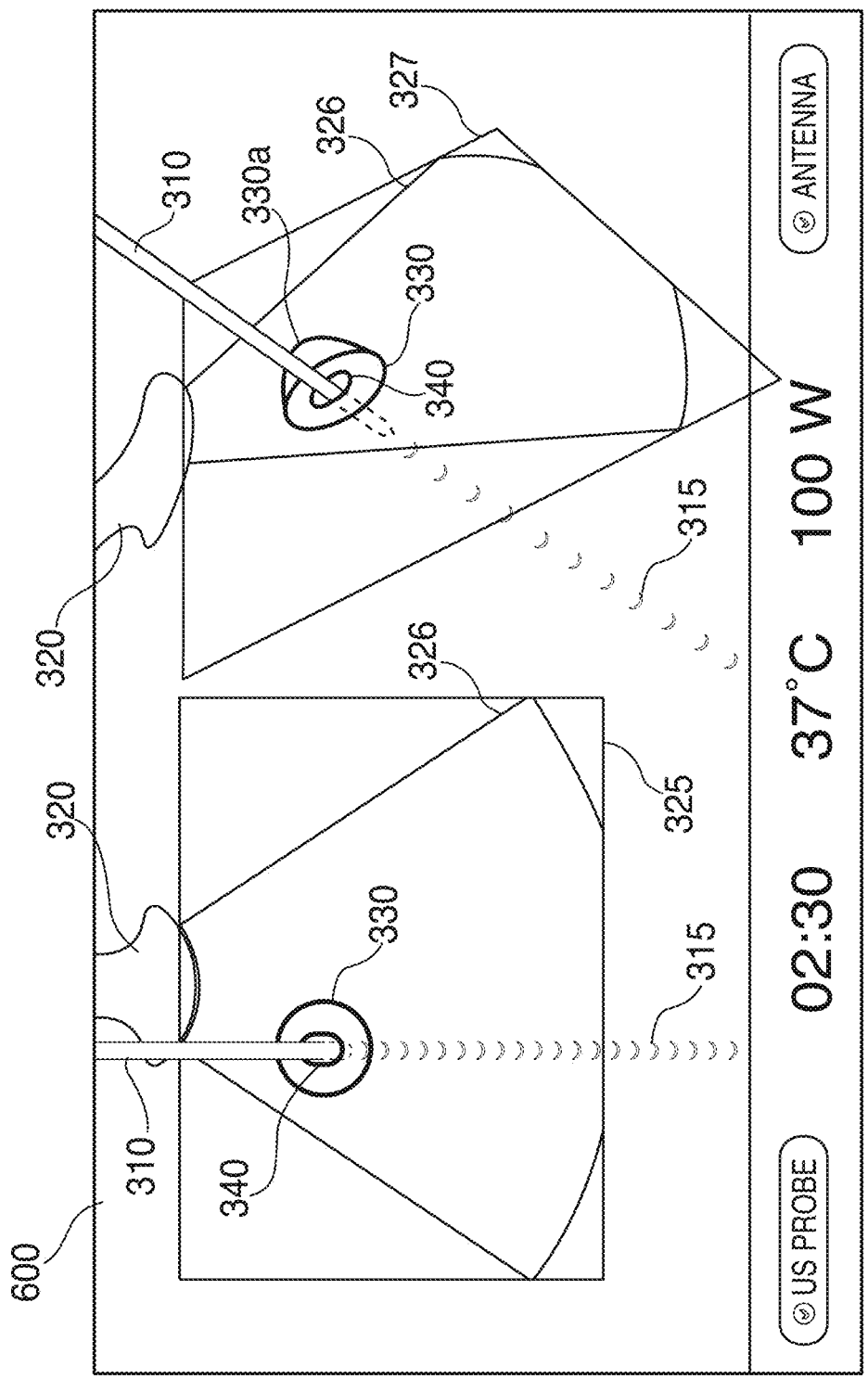
FIG. 6A is an illustration of another example graphical user interface which may be used during the procedure phase of a microwave ablation treatment in accordance with an embodiment of the present disclosure.

With reference to FIG. 6A, GUI 600 includes graphical representation of an ablation antenna 310 corresponding to ablation probe 130, a graphical representation of an ultrasound wand 320 corresponding to ultrasound imager 140, a graphical representation of a trajectory 315 of ablation probe 130, an ultrasound image plane 325 including an ultrasound image 326 based on ultrasound image data captured by ultrasound imager 140, a projected ablation zone indicator 330 showing a projected ablation zone as configured for the current ablation procedure, and an obround 340 indicating the area of intersection between the plane of ablation antenna 310 and ultrasound image plane 325. GUI 600 further includes a perspective view area showing a perspective view of ultrasound wand 320 and an ultrasound image plane 327 based on the position of ultrasound imager 140 within the portion of the EM field configured to be displayed in the perspective view area, as well as the position of ablation antenna 310 relative to ultrasound image plane 327, as described above with reference to FIG. 3E. Because ultrasound image plane 327 is displayed in a perspective view according to the position of ultrasound imager 140, projected ablation zone indicator 330 may be displayed according to a three-dimensional perspective of the projected ablation zone, such as by a dome 330a and/or a sphere (as shown in FIG. 6D).

Figure 6B:
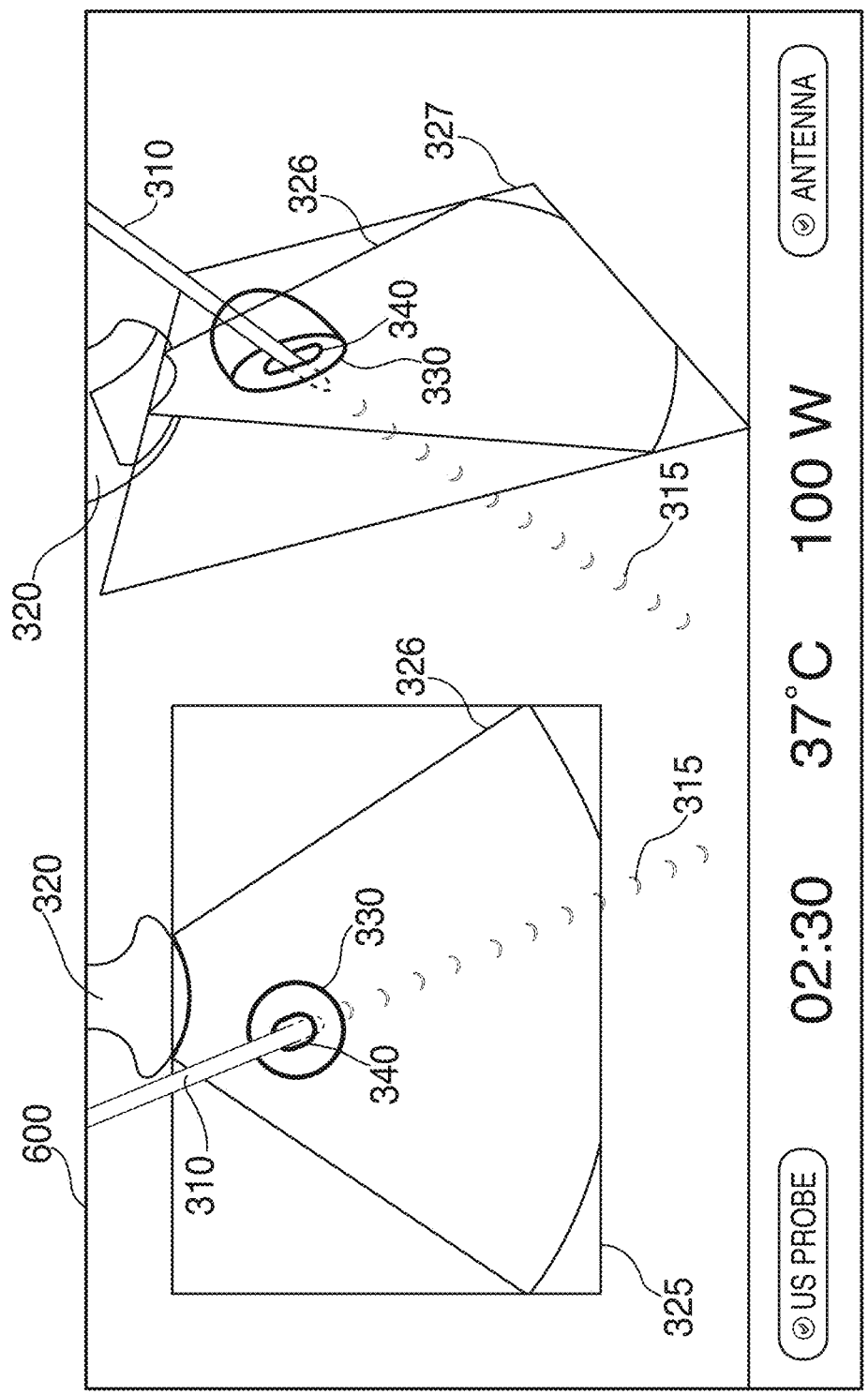
FIG. 6B is an illustration of another example graphical user interface which may be used during the procedure phase of a microwave ablation treatment in accordance with an embodiment of the present disclosure.

FIG. 6B shows another example GUI 600 generated by user interface 218 which may be presented by computing device 100 on display 206 and/or display 110. As shown in FIG. 6B, GUI 600 displays ultrasound wand 320 and ablation antenna 310 at angles different from FIG. 6A, thereby showing how moving ultrasound imager 140 and/or ablation probe 130 within the EM field may result in different output on GUI 600.

Figure 6C:
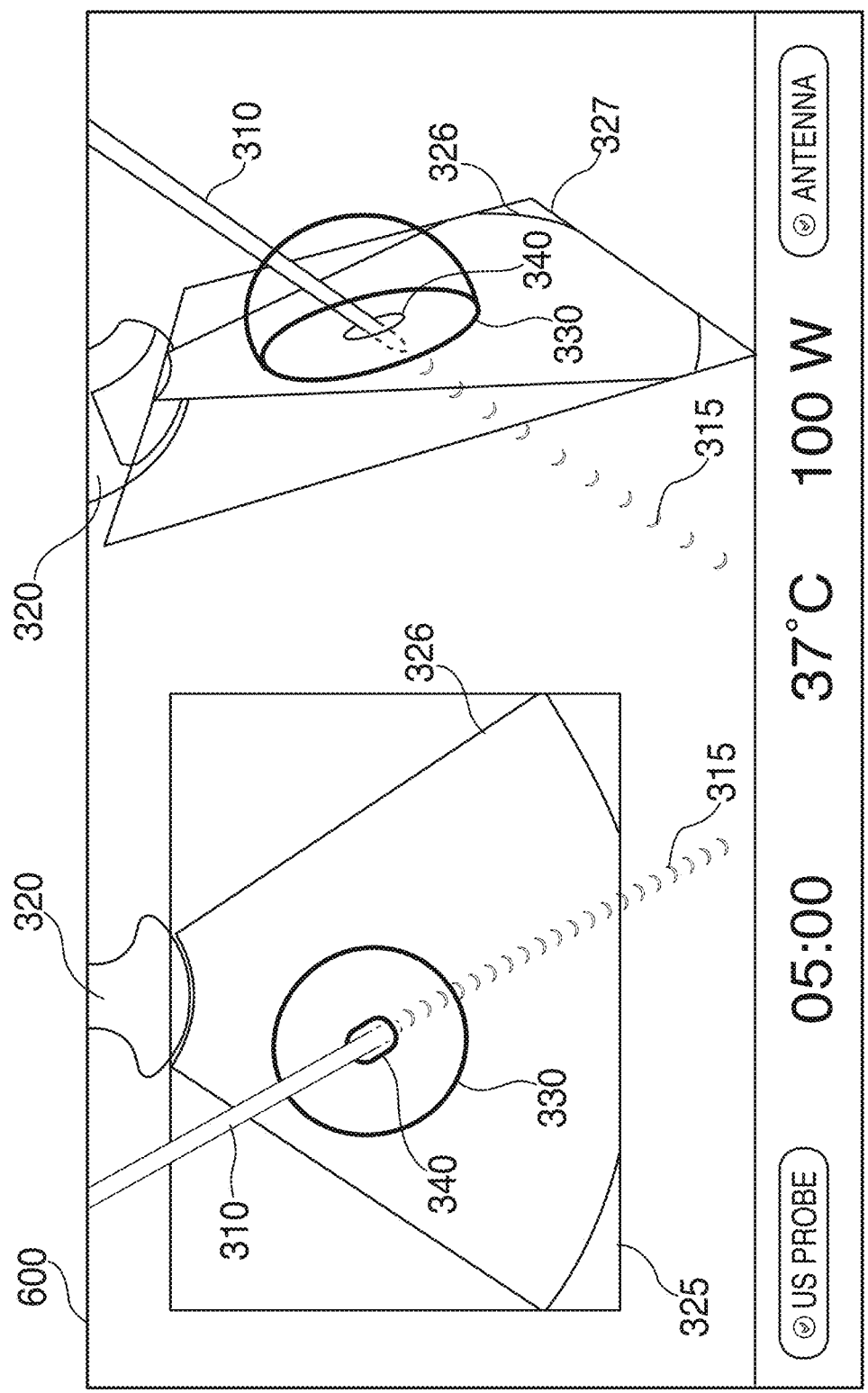
FIG. 6C is an illustration of another example graphical user interface which may be used during the procedure phase of a microwave ablation treatment in accordance with an embodiment of the present disclosure.

FIG. 6C shows yet another example GUI 600 generated by user interface 218 which may be presented by computing device 100 on display 206 and/or display 110. As shown in FIG. 6C, GUI 600 displays ablation zone indicator 330 according to different settings and/or at a different time during the ablation procedure, for example, after more time has elapsed.

Figure 6D:
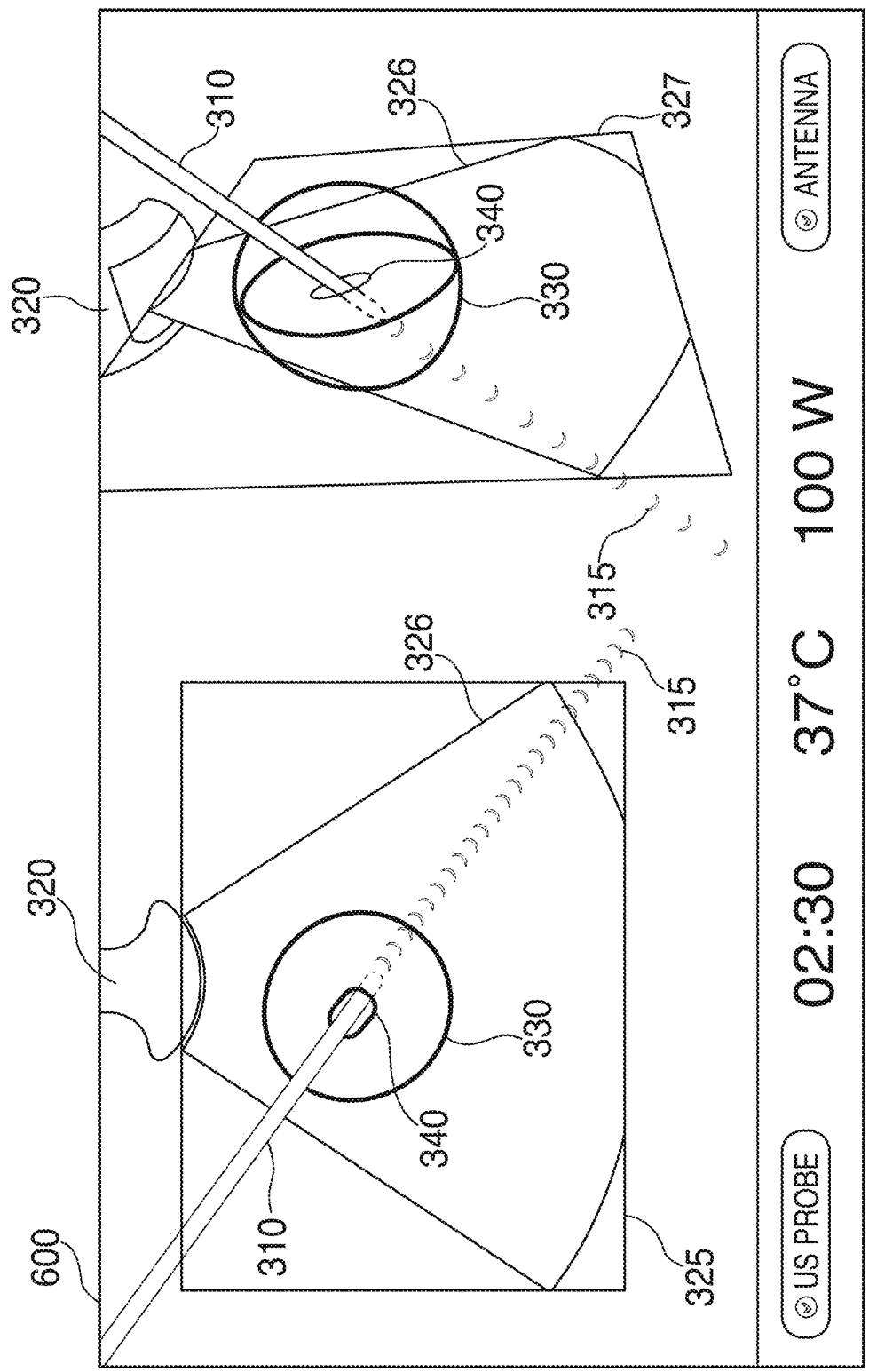
FIG. 6D is an illustration of another example graphical user interface which may be used during the procedure phase of a microwave ablation treatment in accordance with an embodiment of the present disclosure.

FIG. 6D shows yet another example GUI 600 generated by user interface 218 which may be presented by computing device 100 on display 206 and/or display 110. As shown in FIG. 6D, GUI 600 displays ablation zone indicator 330 as a spherical shape centered on the ablation antenna 310.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A system for image-guided ablation antenna placement, the system comprising:
   an electrosurgical generator configured to generate electrosurgical energy;

an ablation probe configured to couple to the electrosurgical generator and deliver electrosurgical energy to tissue;

a position tracking system configured to generate tracking data corresponding to positions of the ablation probe and an imaging device; and a computing device including a processor and a memory storing instructions which, when executed by the processor, cause the computing device to:
receive microwave ablation procedure configuration settings;
receive image data from the imaging device;
receive the tracking data from the position tracking system;
determine a trajectory of the ablation probe based on the tracking data; and
generate a graphical user interface displaying a representation of the ablation probe in relation to an image plane of the image data based on the tracking data from the position tracking system and an ablation progress indicator displaying a perspective view of progress of a size of an ablation zone as an ablation procedure is performed, wherein the computing device is programmed to continually adjust a display of the image plane based on the position of the imaging device.

2. The system of claim 1, wherein the imaging device is an ultrasound imaging device configured to generate ultrasound images.

3. The system of claim 1, wherein the instructions further cause the computing device to:
determine a projected ablation zone based on the received microwave ablation procedure configuration settings; and
show the projected ablation zone in the graphical user interface.

4. The system of claim 1, wherein the instructions further cause the computing device to:
determine whether the position or orientation of the ablation probe has changed; and
update the displayed representation of the ablation probe if it is determined that the position or orientation of the ablation probe has changed.

5. The system of claim 1, wherein the instructions further cause the computing device to:
determine whether the position or orientation of the imaging device has changed; and
generate an updated graphical user interface displaying an updated position or orientation of the image plane if it is determined that the position or orientation of the imaging device has changed.

6. The system of claim 1, wherein the instructions further cause the computing device to:
determine an intersection point between the ablation probe or a trajectory of the ablation probe and the image plane; and
display an indicator corresponding to the intersection point between the ablation probe or the trajectory of the ablation probe and the image plane.

7. The system of claim 6, wherein the indicator is an obround shape showing an angle and directionality of the intersection point between the ablation probe and the image plane.

8. The system of claim 1, wherein the graphical user interface further displays a trajectory of the ablation probe, the trajectory having a length approximately equal to a length of the ablation probe.

9. The system of claim 1, wherein the graphical user interface displays the trajectory of the ablation probe and the representation of the ablation probe as outlines such that the image data displayed is not obscured.

10. A method of generating a graphical user interface for use during image-guided ablation antenna placement, the method comprising:
receiving microwave ablation procedure configuration settings;
receiving image data from an imaging device;
receiving tracking data corresponding to positions of an ablation probe and the imaging device from a position tracking system;
determining a trajectory of the ablation probe based on the tracking data;
displaying a representation of the ablation probe in relation to an image plane of the image data based on the tracking data from the position tracking system and an ablation progress indicator displaying a perspective view of progress of a size of an ablation zone as an ablation procedure is performed; and
continually adjusting a display of the image plane based on the position of the imaging device.

11. The method of claim 10, further comprising:
determining a projected ablation zone based on the received microwave ablation procedure configuration settings; and
displaying the projected ablation zone.

12. The method of claim 10, wherein the imaging device is an ultrasound imaging device.

13. The method of claim 10, further comprising:
determining whether the position or orientation of the ablation probe has changed; and
updating the displayed representation of the ablation probe if it is determined that the position or orientation of the ablation probe has changed.

14. The method of claim 10, further comprising:
determining whether the position or orientation of the imaging device has changed; and
displaying an updated position or orientation of the imaging device if it is determined that the position or orientation of the imaging device has changed.

15. The method of claim 10, further comprising:
determining an intersection point between the ablation probe or a trajectory of the ablation probe and the image plane of the image data; and
displaying an indicator corresponding to the intersection point between the ablation probe or the trajectory of the ablation probe and the image plane of the image data.

16. The method of claim 15, wherein the indicator is an obround shape showing an angle and directionality of the intersection point between the ablation probe and the image plane of the image data.

17. The method of claim 10, wherein the trajectory has a length approximately equal to a length of the ablation probe.

18. The method of claim 10, further comprising displaying the representation of the ablation probe as outlines such that the image data is not obscured.

19. A non-transitory computer-readable storage medium storing instructions which, when executed by a processor, cause the processor to:
receive microwave ablation procedure configuration settings;
receive image data from an imaging device;
receive tracking data corresponding to positions of an ablation probe and the imaging device from a position tracking system;

determine a trajectory of the ablation probe based on the tracking data;
display a representation of the ablation probe in relation to an image plane of the image data based on the tracking data from the position tracking system and an ablation progress indicator displaying a perspective view of progress of a size of an ablation zone as an ablation procedure is performed; and
continually adjust a display of the image plane based on the position of the imaging device.

* * * * *